(12) United States Patent
Shalon (10) Patent No.: US 9,034,193 B2
(45) Date of Patent: May 19, 2015

(54) SYSTEM AND METHOD FOR CONTROLLING WATER QUALITY IN A RECREATIONAL WATER INSTALLATION

(75) Inventor: Tadmor Shalon, Palo Alto, CA (US)

(73) Assignee: Waterpods, Inc., Palo Alto, CA (US)

( * ) Notice: Subject to any disclaimer, the term of this patent is extended or adjusted under 35 U.S.C. 154(b) by 0 days.

(21) Appl. No.: 13/983,971

(22) PCT Filed: Feb. 9, 2012

(86) PCT No.: PCT/IB2012/050586
§ 371 (c)(1),
(2), (4) Date: Aug. 6, 2013

(87) PCT Pub. No.: WO2012/107895
PCT Pub. Date: Aug. 16, 2012

(65) Prior Publication Data
US 2013/0313204 A1    Nov. 28, 2013

Related U.S. Application Data

(60) Provisional application No. 61/457,243, filed on Feb. 10, 2011.

(51) Int. Cl.
*E04H 4/12* (2006.01)
*C02F 1/00* (2006.01)
(Continued)

(52) U.S. Cl.
CPC .............. *E04H 4/1281* (2013.01); *C02F 1/006* (2013.01); *G01N 33/18* (2013.01); *C02F 1/008* (2013.01);
(Continued)

(58) Field of Classification Search
CPC ............ C02F 1/68; C02F 1/685; C02F 1/687; C02F 1/688; C02F 1/006; C02F 1/008; C02F 1/76; C02F 1/683; C02F 1/686; C02F 2101/38; C02F 2103/42; C02F 2209/02; C02F 2209/04; C02F 2209/06; C02F 2209/008; C02F 2209/29; C02F 2209/42; C02F 2303/04; E04H 4/00; E04H 4/14; E04H 4/16; E04H 4/1209; E04H 4/1281; G05B 19/00; G05B 19/02; G05B 19/0421; G05B 19/0423; G05B 19/0425; G05B 19/0426; G05B 19/042; G01N 33/18; B26D 5/00; B26D 5/06; B26D 5/086; B26D 5/20; B26D 5/24; B26D 5/42; B26D 7/02; B65B 41/12; B65B 61/00; B65B 61/06; B65B 61/02; B65B 61/007; B65B 61/005; B65B 61/065; B65B 61/08; B65B 61/10; B65B 61/12; B65B 61/18; B65B 69/00; B65B 69/0008; B65B 69/0033
USPC ................................ 222/52, 63, 94, 325, 196
See application file for complete search history.

(56) References Cited

U.S. PATENT DOCUMENTS 4,769,137 A     9/1988   Powell, Jr.
4,780,197 A  *  10/1988  Schuman ...................... 210/136
(Continued)

FOREIGN PATENT DOCUMENTS

JP         3089916 B2 *  9/2000  ................ F24H 1/00

OTHER PUBLICATIONS

Translated abstract of Sato patent from espacenet (JP3089916B2).*
(Continued)

*Primary Examiner* — Lucas Stelling
*Assistant Examiner* — Rohit K Dewan
(74) *Attorney, Agent, or Firm* — Shay Glenn LLP (57) ABSTRACT

A system for monitoring water chemistry of a recreational water installation includes a sensor configured to detect bather load in the recreational water installation and a controller configured to determine a required adjustment to the water chemistry of the recreational water installation based upon the detected bather load.

16 Claims, 6 Drawing Sheets

(51) Int. Cl.
  G01N 33/18 (2006.01)
  C02F 1/68 (2006.01)
  C02F 1/76 (2006.01)
  C02F 101/38 (2006.01)
  C02F 103/42 (2006.01)

(52) U.S. Cl.
  CPC ............... C02F 1/687 (2013.01); *C02F 1/683* (2013.01); *C02F 1/686* (2013.01); *C02F 1/76* (2013.01); *C02F 2101/38* (2013.01); *C02F 2103/42* (2013.01); *C02F 2201/009* (2013.01); *C02F 2209/008* (2013.01); *C02F 2209/02* (2013.01); *C02F 2209/06* (2013.01); *C02F 2209/29* (2013.01); *C02F 2209/42* (2013.01); *C02F 2303/04* (2013.01)

(56) References Cited

U.S. PATENT DOCUMENTS

| | | | |
|---|---|---|---|
| 4,825,528 A | 5/1989 | Nicholson et al. | |
| 5,476,116 A | 12/1995 | Price et al. | |
| 5,662,795 A | 9/1997 | Pickens et al. | |
| 5,985,155 A * | 11/1999 | Maitland | 210/739 |
| 6,238,553 B1 | 5/2001 | Lin | |
| 6,309,538 B1 * | 10/2001 | Khan | 210/85 |
| 7,292,898 B2 * | 11/2007 | Clark et al. | 700/9 |
| 7,409,853 B2 | 8/2008 | Biberger et al. | |
| 8,007,664 B2 | 8/2011 | Reed et al. | |
| 2001/0045380 A1 | 11/2001 | Khan | |
| 2002/0056689 A1 | 5/2002 | Shim et al. | |
| 2007/0094817 A1 | 5/2007 | Stoltz et al. | |
| 2007/0138109 A1 * | 6/2007 | Tufano et al. | 210/748 |
| 2008/0094235 A1 * | 4/2008 | Brochu et al. | 340/635 |
| 2009/0218296 A1 * | 9/2009 | King et al. | 210/744 |
| 2011/0139727 A1 * | 6/2011 | Hui | 210/749 |

OTHER PUBLICATIONS

Wojtowicz, Chemistry of Nitrogen Compounds in Swimming Pool Water (2001).*
Bullock, Chapter 5—Materials and Methods (2003).*
OnBalance, The Role of CO2 in Pool Water (2006).*

* cited by examiner

SYSTEM AND METHOD FOR CONTROLLING WATER QUALITY IN A RECREATIONAL WATER INSTALLATION

FIELD AND BACKGROUND OF THE INVENTION

The present invention relates to a system and method for controlling the quality of water in a recreational water installation such as spa, hot tub or pool.

The water quality of a recreational water facility depends on sanitation and chemical balance. In recreational water facilities where the water volume is fairly small, such as spas and hot tubs, proper sanitation and chemical balance largely depend on the number of bathers and the duration of use.

In pools, the challenges of keeping the water properly sanitized and balanced efficiently while maximizing user experience are magnified due to the larger volume of water and the affect on water quality of environmental conditions such as rain, wind and sun.

Bathers introduce most of the waste into the spa. This waste includes urea, sweat, bacteria and dead skin that the sanitizer must rapidly oxidize in order to prevent bacteria from proliferating and forming biofilms that are very difficult to eradicate. The number of bathers and length of use determine oxidizer consumption in the spa. For example, a typical 350 gallon spa will require 11 grams of dichlor sanitizer following use by two bathers soaking for 20 minutes while the same spa will require only about 1 g per day when not in use. Bathers prefer water that feels soft and smells 'clean' which requires low levels of sanitizer (typically 2-5 ppm). Thus, in spas, sanitizer should be applied immediately after use to oxidize the waste and then be kept at low levels so that the water feels 'chemical free' when the user enters the spa again. This is the challenge of spa maintenance and the reason it is difficult to properly sanitize the spa with steady state or scheduled introduction of a sanitizer.

Free chlorine is the most popular EPA recognized sanitizer. Chlorine is effective in killing bacteria and viruses leading to water turbidity if used at the right amount (1-4 ppm) and time. Chlorine sanitizer also oxidizes biological residues introduced by the users leading to foaming and produces chloramines that give the spa its 'chlorine' smell.

Proper maintenance of pH is also important for safety and comfort of spa users. Sweat, sanitizer oxidation, and aeration jets affect pH and lower alkalinity. The pH needs to be raised to maintain appropriate levels for the sanitizer to be effective and the water to feel comfortable. Sanitation products such as bromine tablets (Bromo Chloro Dimethyl MH—BCDMH), dichlor tablets both dispensed from a floater for sanitizer background level maintenance, biguanides without chlorine, and heavy metal filters (not EPA approved) all have issues requiring user intervention, high background sanitizer levels, costs or other side effects.

While reducing the present invention to practice, the present inventor has devised a sanitation system that can provide use-responsive sanitation of a recreational water facility such as spa. The present system can be used to maintain fresh smelling, comfortable spa water with minimal user intervention and while minimizing the use of sanitizers and other chemicals.

SUMMARY OF THE INVENTION

According to one aspect of the present invention there is provided a system for monitoring and optionally regulating water chemistry of a recreational water installation comprising at least one sensor for detecting usage of the recreational water installation and indicating and/or regulating water chemistry based on the usage.

According to further features in preferred embodiments of the invention described below, the at least one sensor is configured for identifying a number of individuals using the recreational water installation and/or duration of use.

According to still further features in the described preferred embodiments the at least one sensor is selected from the group consisting of an accelerometer, a microphone and a photoelectric sensor.

According to still further features in the described preferred embodiments the recreational water installation is a spa.

According to still further features in the described preferred embodiments the sensor is housed in a free floating device.

According to still further features in the described preferred embodiments the system provides instructions for regulating the water chemistry based on an input from the at least one sensor.

According to still further features in the described preferred embodiments the system includes a dispenser for dispensing at least one chemical for regulating water chemistry.

According to still further features in the described preferred embodiments the dispenser is configured for dispensing one or more dose units of the at least one chemical.

According to still further features in the described preferred embodiments the dose units are in the form of a powder, a pellet, a liquid or a gel.

According to still further features in the described preferred embodiments the at least one chemical is selected from the group consisting of dichlor, lithium hypochlorite, calcium hypochlorite.

According to still further features in the described preferred embodiments the system further comprises a water chemistry sensing device.

According to still further features in the described preferred embodiments the water chemistry sensing device is an oxidation reduction potential electrode, a colorimetric microfluidic device or colorimetric strips/pads.

According to still further features in the described preferred embodiments the system is further capable of estimating changes in water chemistry during non-use periods.

According to still further features in the described preferred embodiments the system is further capable of removing an unwanted chemical present in the water.

According to still further features in the described preferred embodiments the removing is effected by releasing a composition capable of sequestering the chemical.

According to still further features in the described preferred embodiments the unwanted chemical is CYA.

According to still further features in the described preferred embodiments the composition includes melamine.

According to still further features in the described preferred embodiments the system further comprises wireless communication capabilities.

According to still further features in the described preferred embodiments the system is capable of communicating data relating to usage, chemistry or condition of the recreational water installation to a user or a server.

According to another aspect of the present invention there is provided a system for dispensing one or more chemicals into water of a recreational water installation comprising: (a) a plurality of chemical dose units each including a dose of the chemical contained in a water impermeable package; and (b) a dispensing unit being capable of holding and individually dispensing the chemical dose units, the dispensing unit including a mechanism for physically disrupting the water impermeable package of a chemical dose unit.

According to yet another aspect of the present invention there is provided a system for monitoring and optionally regulating water chemistry of a recreational water installation comprising a float and an accelerometer or gyroscope for measuring a movement of the float.

According to still further features in the described preferred embodiments the float is mounted on a pivot and the accelerometer or gyroscope measures a pivoting angle of the float.

According to still another aspect of the present invention there is provided a system for monitoring and optionally regulating water chemistry of a recreational water installation comprising an open tube with a first end positioned in water of the recreational water installation and a second end open to air and a microphone for measuring a resonant frequency of the tube.

The present invention successfully addresses the shortcomings of the presently known configurations by providing a system for automatically monitoring and adjusting water chemistry in a recreational water installation such as a spa.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software. For example, as hardware, selected steps of the invention could be implemented as a chip or a circuit. As software, selected steps of the invention could be implemented as a plurality of software instructions being executed by a processing unit using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a system which can be used for monitoring and regulating the water quality of a recreational water facility. Specifically, embodiments of the present invention can be used to monitor usage of a spa and regulate the water quality thereof based on monitored usage.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention relates to a system which can monitor water chemistry in a recreational body of water and optionally report and/or automatically (closed loop) adjust such chemistry. As used herein, the phrase "water chemistry" refers to the level and type of chemicals present in the water and in particular chemicals that influence the pH, salinity and sanitation of the water. Such chemicals can include, but are not limited to sanitizers (e.g. chlorine releasing compounds) and products thereof, pH influencing chemicals and chemicals that are products of interaction of such chemicals with bacteria, human subjects etc.

The system of the present invention includes one or more devices that can be attached to a wall of the spa or a component thereof (e.g. pump, filter) or it can be designed to float freely in the spa water. The system includes sensor(s) and software designed for automatically monitoring and determining spa usage to thereby assess the condition of the spa water. The system further includes hardware for communicating maintenance instructions to the user, which can include, but are not limited to:

(i) type and quantity of sanitizer to add in order to maintain optimal sanitation;

(ii) type and quantity of additional chemicals such as pH modifiers based on spa usage;

(iii) replacement of spa water based on use and industry recommendations; and/or (iv) replacement or cleaning of filter based on use.

By monitoring spa usage and providing periodic instructions to the user, the present system frees the user from guessing or calculating maintenance needs thus providing an easy and cost effective approach for maintaining spa water safe and comfortable for use.

Figure 1A:
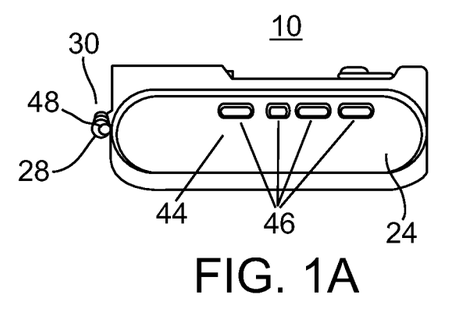
FIGS. 1A-C illustrate top (FIG. 1A), side (FIG. 1B) and front (FIG. 1C) views of the system of the present invention.
Figure 1B:
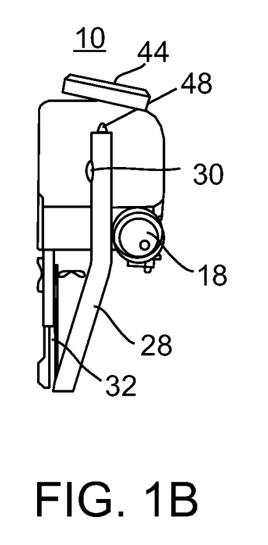
Figure 1C:
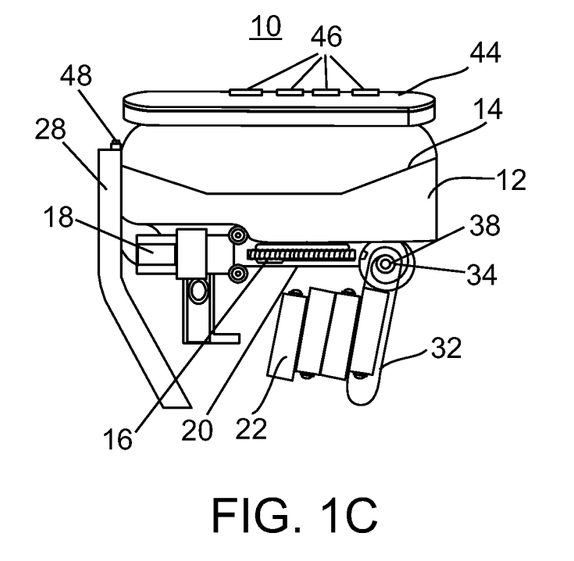

FIGS. 1a-c illustrate one embodiment of the present system which is referred to herein as system 10. It will be appreciated that although the descriptions provided hereinbelow are made with reference to spas/hot tubs, system 10 also finds use in other recreational bodies of water such as pools and the like.

System 10 includes a housing (not shown) for containing the various functional components of system 10 and for isolating electronics and chemicals from the water of the spa. The housing can be fabricated from a polymer [e.g. Acrylonitrile butadiene styrene (ABS)] shell which provides a water tight seal for batteries, electronics and motors and is secured with screws and/or adhesive tabs to the spa wall. The Housing can be configured to provide buoyancy in a free floating configuration of system 10.

System 10 includes a chemical dispensing unit 12 which stores and dispenses one or more chemicals such as sanitizer and pH balancing agent.

Preferably, such dispensing is effected from a cartridge containing bulk powdered chemical by using a mechanism 16 that includes a known volume sliding dispenser which loads dry powder from the cartridge and dispenses it into the water (while keeping the bulk powder dry under all conditions).

The internal volume of dispensing unit 12 is configured such that a chemical contained therein is forced towards the center of dispensing unit 12 where dispensing occurs. For example, and as shown in FIG. 1c, dispensing unit 12 is internally sloped (as shown by 14), such that a chemical in liquid or powder form is gravitationally forced towards the middle when system 10 is upright (when in use).

Alternatively, chemical dispensing unit can include chemical dose units each individually packaged in a water impermeable wrap. The system can further incorporate a mechanism (e.g. movable blade) for physically disrupting the wrap material (not shown) prior to dispensing thus allowing immediate dispersal of the chemical in the spa water.

As is mentioned above, dispensing from dispensing unit 12 is controlled by a mechanism 16 which can include a motor 18 and a worm drive 20. Power for motor 18, as well as other components, is provided by batteries 22. Batteries 22 can be recharged via a solar panel 24 (shown in FIG. 1a) or via corded connection to power source (e.g. AC power outlet). The operation of mechanism 16 is described in further detail hereinbelow.

Based on the condition of the water, system 10 can dispense one or more dose units of a specific chemical whether from bulk powder, hydrated powder (dispensed as a solution) or from individually wrapped dose units.

System 10 further includes a sound tube 28 and a microphone 30. Microphone 30 is coupled to the top of sound tube 28 whose open bottom end is immersed in the water. The resonant frequency of sound tube 28 changes as a function of water level or effective free air length of the tube. As the water rises, the resonant frequency increases. The ambient sounds or an injected white noise generated from a speaker 48 is recorded by the microphone and processed via a FFT to measure the resonant frequencies which are directly related to the water level. As is further described hereinbelow, measuring additional background frequencies characteristic of motors, pumps, or turbulent water can provide information on whether the spa pumps or jets are on.

System 10 can alternatively or additionally include a float 32 which is mounted on a pivot 34. An accelerometer (or gyroscope) 38 is mounted on float 32 near pivot 34. Accelerometer 38 is preferably a three-axis accelerometer (e.g. a FreeScale MMA8453). As the water level in the spa rises, float 32 pivots and accelerometer 38 (sensing gravity acts as inclinometer) determines a change in an angle of float 32. Such a change in water level can be used to detect Spa use and estimate the number of bathers in the spa (as is further described hereinbelow).

Acceleration and movement of the floating arm caused by water movement as detected by accelerometer 38 can also be used to determine use of jets or air bubbles as well as the filter cycle of the spa. Additional axis of accelerometer 38 can be used to determine if system 10 is securely attached to the spa wall. The dispensing cycle can be disabled if accelerometer 38 data indicates that system 10 is not in the correct orientation (e.g. detached from wall and free floating in the spa or being handled by the user).

Float 32 is also used to determine and alert the user if there's too little or too much water in the spa or if the water level is higher than the dispensing port in order to insure that the dry powder stored in system 10 does not come into contact with water.

Accelerometer 38 data can also be used to determine whether the spa cover is on or off by detecting vibrations induced by spa cover removal or replacement.

In the free floating configuration of system 10, accelerometer patterns (e.g. within 1 Hz oscillation resonant frequency) can be further analyzed to determine the natural oscillation of system 10 in water (which is proportional to its mass) and thus determine the remaining chemical content in dispensing unit 12.

System 10 can further include water temperature sensors and light sensors which can be used to determine spa water temperature, sunlight exposure as well as other parameters. Light and temperature sensor data processing by the present system is further described hereinbelow.

System 10 further includes a user interface 44 which includes controls 46, and optionally a display (not shown). User interface 44 can allow the user to manually control the processing unit of system 10 which controls chemical dispensing according to input received from water level sensor, internal timer, temperature and state of cover. User interface can also be used to enter, edit or monitor the number of spa users and chemical dispensing cycles.

System 10 can further include a communication unit which can be used to wirelessly (e.g. WiFi, Bluetooth) connect system 10 to a computational device such as a computer or a smartphone/tablet. Such communication can allow the user (or an agent thereof) to monitor the system (directly or via the Internet), control it, make and input measurements, and order chemical supplies.

Figure 2:
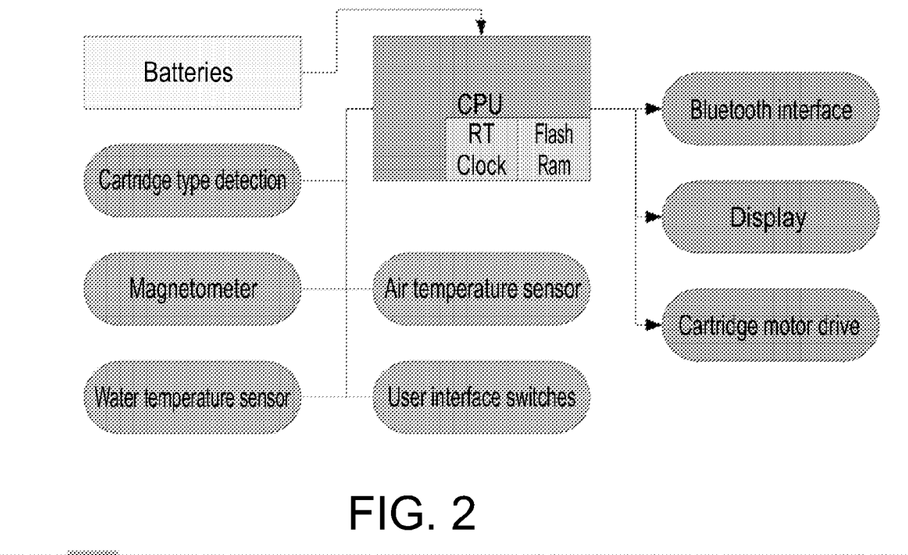
FIG. 2 illustrates the various functional components of the system of the present invention.

A functional relationship between components of one configuration of system 10 is illustrated in FIG. 2.

Sensor Data

As is mentioned hereinabove, float 32 includes accelerometer 38 which functions as an inclinometer to determine a change in the angle of float 32 with the rising water level.

Figure 3:
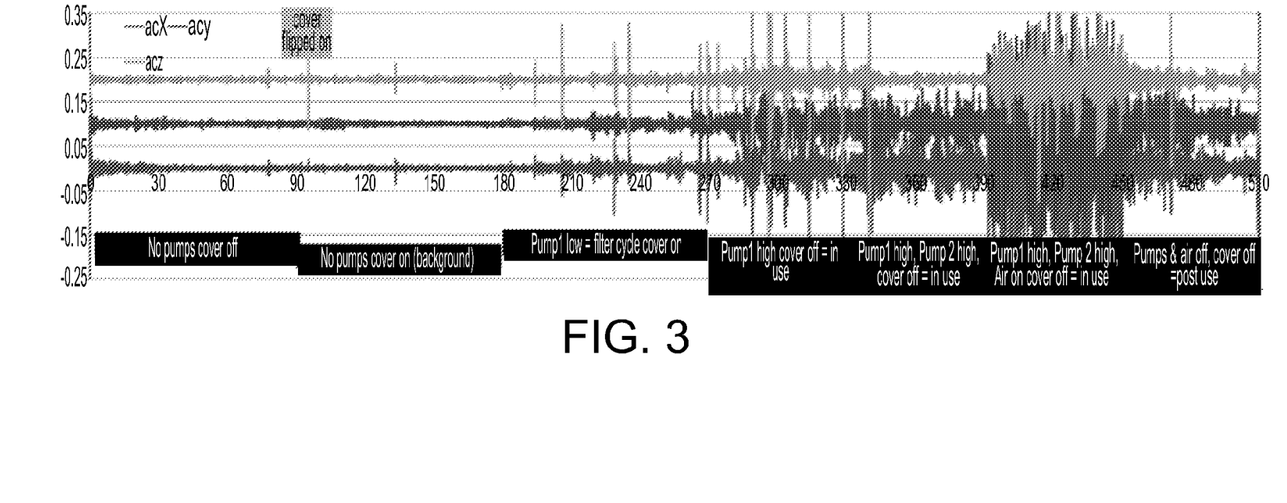
FIG. 3 illustrates the accelerometer derived data in response to different spa conditions.
Figure 4:
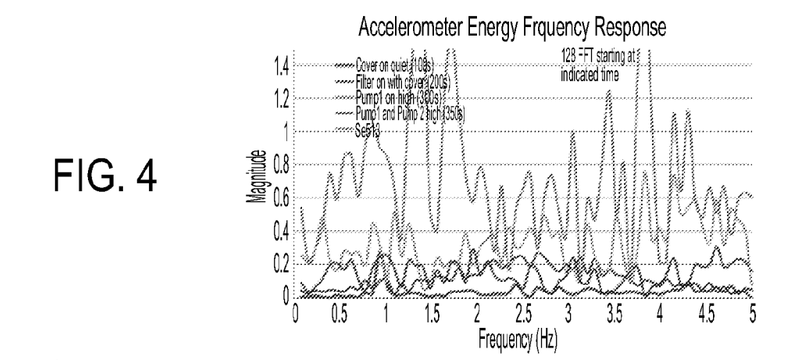
FIG. 4 illustrates the frequency components of the accelerometer spa data.

The data provided by accelerometer 38 can be used to deduce the number of bathers in the spa (See FIGS. 3-4). In a 400 gallon spa, a typical adult user will cause approximately a 1 cm rise in water level. Such a rise will lead to a measurable tilt and change in angle in float 32 and generation of accelerometer data. The processor of system 10 can automatically calibrate itself for each spa by monitoring the discrete changes in water level and use this information to ascertain the size (based on the amount of discrete water level change from the previous level) and number of individuals using the spa at any time.

System 10 can be attached to the side of the spa with a string or a rod or ride up and down a rod affixed to the spa's side via suction cups. The accelerometer pattern of the time between changes in direction is a further indication of the number of users since the effective spa free floating area decreases with the number of users who typically sit near its edges.

System 10 can include sensors capable of ultrasound or infrared light measurements. Such sensors can measure the distance from system 10 to the bottom of the spa and thus determine water level and thus spa usage. Other sensors for measuring water levels can measure an optical encoder on a fixed vertical pole on which system 10 can float up or down.

Spa use measurements can also be effected using a pressure sensor such as FreeScale MPXV7007DP which is connected to a tube with its open end submerged in the water. As users enter the spa, the water level rises, the pressure in the tube increases, and the increased voltage from the sensor is read by the embedded microprocessor. Alternatively, a pressure sensor can be sealed in a water and vapor impermeable bladder (e.g. a metalized aluminum heat sealed film) above the water with a similar bladder connected to its differential pressure port and located below the water. Alternatively the water submerged bladder contains an open cell foam to retain its shape. As the water level rises, the differential pressure between the two sealed bladders changes and a resulting voltage is read and interpreted by the microprocessor.

Figure 5A:
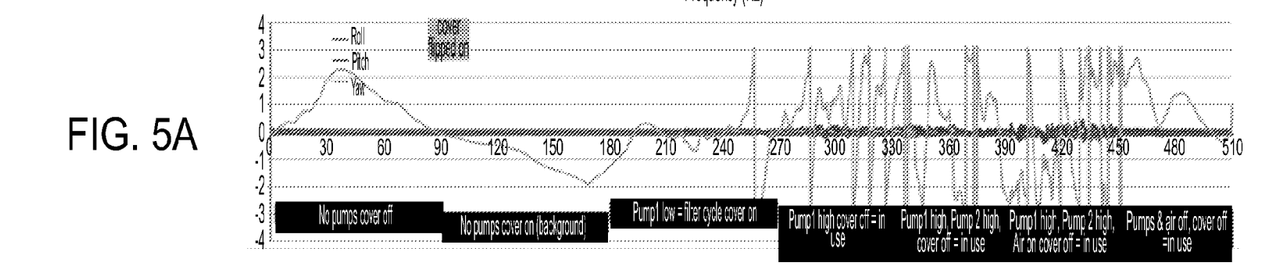
FIGS. 5A-B illustrate magnetometer (FIG. 5A) and gyroscope (FIG. 5B) data obtained in response to different spa conditions.
Figure 5B:
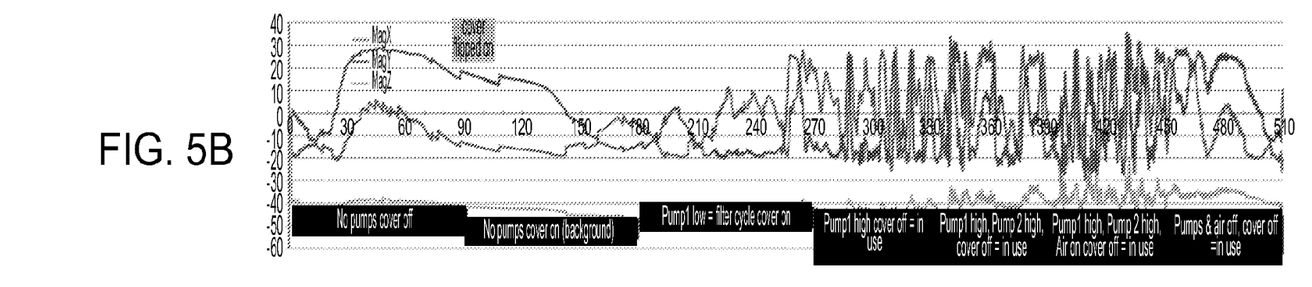

A magnetometer or gyroscope can also be used to make similar spa use measurements as described in FIG. 5a-b. A magnetometer measurement from a magnet affixed to the spa can determine the number of users in the spa where each adult typically raises the average spa water by nearly 1 cm.

Alternatively, a floating reflector or magnet can be placed in a vertical open tube where the appropriate sensor can determine the distance to the floating target. Such distance will be proportional to the water level in the spa and thus to the number of bathers using it.

System 10 can be put into a sleep mode (low power consumption mode) and wake up in response to motion detected by the accelerometer or gyroscope. This allows system 10 to substantially reduce power consumption in the long intervals between detected water motion and thus conserve battery power.

As is mentioned above, system 10 also utilizes a sound tube 28 and a microphone 30. The resonant frequency of tube 28 changes as a function of water level or effective free air length of tube 28. As the water rises, the resonant frequency increases. For example, when an adult enters a typical 350 gallon spa, the water level rises by 1 cm and the air in the sound tube changes from 10 to 11 cm which can be detected by the resonant frequency of the sound tube changing from 770 Hz to 846 Hz.

The processor measures the accumulated duration of the use of the jets and bubbles as described above and together with bather load and the volume of the spa (as entered by the user via user interface 44), determines and alerts the user when the pH needs to be checked and adjusted.

Bather load is also used to alert the user when to clean the filter or change the water.

A log of bather load and use patterns combined with the amount of sanitizer dispensed is analyzed by system 10 to predict and alert the user of when to expect to replenish the sanitizer in dispensing unit 12.

System 10 can also include sensors to detect air temperature and or surface water temperature. Such temperatures change when the spa cover is removed in preparation for use. And as such, detection of such change can be indicative of spa cover removal. For example, removal of a spa cover can lead to a rapid temperature drop in a typical spa with water temperature of 103° F. and air temperature of 53° F.

Water temperature sensors can also be used to determine the saturation level of the chemistry kept in hydrated form in system 10 to allow the device to calculate the precise volume of solution needs to be dispensed to the spa water.

Additional light sensors can be used to determine whether the spa is covered or not. In a pool environment, the light sensors and the temperature sensors can be used to detect sun load on the pool which is a factor in the loss of sanitizer and make up the lost sanitizer in response to the environmental factors. In addition, the motion of system 10 which is detected as described above can be used to estimate wind and environmental debris deposited into a pool and correspondingly release appropriate amounts of a sanitizer to compensate for it.

Use patterns are recorded by system 10 and are used along with spa volume measurements to determine when and how to dose the spa. Total use time is proportional to the amount of sanitizer needed to oxidize the waste users generated in the spa. A bather use time, the use of jets and the sanitizer use are proportional to the pH adjustments that are needed. Total bather time and the spa volume are proportional to the recommended spa water changes. The application of chemicals can be tracked by system 10 and together with use patterns, system 10 can generate a recommendation of spa maintenance or preferably automatically maintain the correct chemistry of the spa. For example, 9 g of LH will be dispensed for each adult soaking for 20 minutes in the spa. pH check will be recommended for every 8 hours of jet or bubble usage. Water change will be recommended based on spa volume divided by number of user soaks. Filter cleaning will be recommended at twice the rate of water change.

Chemical Dispensing

Dispensing unit 12 can include sealed sanitizer (e.g. chlorine) cartridges. Sanitizer chemistry can be chosen among a dichlor, lithium hypochlorite, bromine/dichlor combination or a non-chlorine oxidizer which are commercially available in the pool and spa industry as are various powder form pH and alkalinity control chemicals. On-demand dispensing of lithium hypochlorite (LH) is presently preferred since it allows effective sanitation of the spa without significant change to the pH or buildup of a other compounds such as cyanuric acid (CYA) that will slow down the activity of the newly dispensed LH or other chemicals such as calcium that would harm the equipment.

When system 10 determines that a dose is needed, motor 18 causes worm drive (pinion) 20 to move a rack that slides a dispensing carriage from its 'fill' position which seals the cartridge to its 'dispense' position where the measured powder drops into the water. The carriage materials is made from a low surface energy plastic that will cause any remaining powder to hydrate and drip into the spa. The processor of system 10 senses the current of motor 18 to determine when it is stalled due to carriage reaching the end of its travel. The current sensed in software can also determine if powder granules are jammed in the sliding dispenser at which time motor 18 reverses the carriage motion temporarily to unjam it. A new cartridge is shipped with the carriage not fully against the end of travel so that the motor can determine this condition from the time it takes it to reach a stalled condition and thus allow system 10 to sense that a new cartridge has been placed into dispensing unit 12. The carriage powder entry and exit holes are configured so that in no carriage position both are open and thus prevent the user from refilling the cartridge or from spa water to contact the dry LH powder stored in the cartridge. In addition, the seal is configured such that any gas build up in the cartridge will vent outside before damaging the cartridge itself.

In another configuration, chlorine can be shipped and stored in a cartridge with granulated powder of a dichlor (sodium dichloro-s-triazinetrione dihydrate) of approximately 700 g which should last for 40 soak hours (2 people using the spa 4 times a week for 20 minutes) or 3.5 months which is the time recommended between water changes for this spa size and use. This offers major advantage in that it offers a concentrated source of sanitizer (over 50% by volume) that remains chemically stable in the hydrated cartridge and can be shipped via commercial services in granulated form (unlike bleach which is offered at about 6% concentration). System 10 pumps spa water into the cartridge and a corresponding amount of concentrated solution of chlorine exists via a small port on the side of the cap. The cap is welded on the cartridge after filling to insure that the powder or liquid cannot be accidentally spilled by the user. The changing buoyancy and transparency of the cartridge allows the user to see how much powder is left at the bottom of the cartridge. System 10 hydrates the granules with spa water when the cartridge is first installed to create a saturated chlorine solution of about 150,000 ppm (adjusted for spa water temperature as measured by system 10) which remains at that concentration as long as there are granules in the cartridge. System 10 can employ a pump with known volume per stroke to pump in a known volume of spa water and thus expel the desired volume of the saturated chlorine out of the cartridge (about 10 ml per 1 ppm in 350 gallon spa).

As is mentioned above, system 10 calculates the precise chlorine concentration needed to be pumped out, preferably in small spurts. This approach for chemical dispensing is advantageous from a safety perspective since active pumping is required to transfer chemicals to the water. System 10 will dispense only when the spa is not in use and anticipates the filter cycle which circulates the chlorine to begin dispensing a precise dose of chlorine which will be quickly consumed by oxidizing the bather's waste. System 10 can further include a power switch to insure against incorrect or mistimes dispensing.

Figure 6:
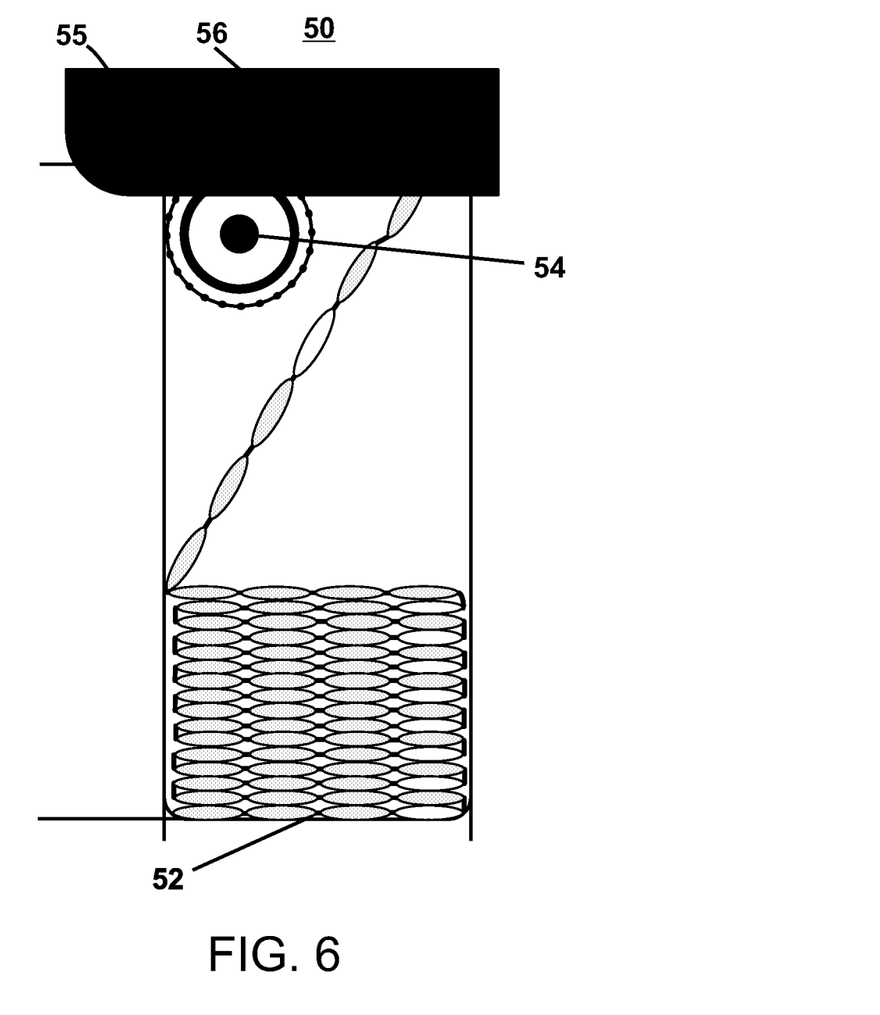
FIG. 6 illustrates a cartridge for storing and dispensing the unit doses utilized by the present system.

In yet another embodiment, chemicals that are very hydroscopic or not unstable in their hydrated form such as lithium hypochlorite can be dispensed automatically as described above or by packaging them into a long strip of small individual packets using a fill/form/seal commercial custom machine with appropriate vapor water barrier polymeric film that can be heat sealed and formed into the packets. Such film can be picked form the following examples: 12 micron PET+ 11 micron aluminum+12 micron PET+75 micron polyethylene; or 12 micron PET+2 ohm per square vapor deposited aluminum+50 micron polyethylene. FIG. 6 illustrates a dispenser cartridge 50 which can be placed into dispensing unit 12. Cartridge 50 includes a strip of packets 52 which moves manually or via a manually or via motor 55 driven pickup reel 54 past packet disruption mechanism 56 (e.g. blade) which disrupts each packets and dispenses its content to the spa water. In order to overcome the impact of high temperature and humidity in the spa on the motor, it can be mounted on a polyethylene structure which is heat sealed to a similar film structure with the shaft protruding through the said structure and sealed via O-ring or a thin bearing packed with lithium grease. A desiccant packet in the sealed structure can further increase the field service life of the motor. Alternatively, the polyethylene in the examples above can be blended with polybutylene and the front and back of each packet can be peeled by the motor drive pulling them apart and the content dispensed in to the water. The motor and the pickup reel can be inside the spa or outside the spa by pulling the empty film through a thin chute between the spa edge and spa cover. The strip of packets can be stored in a roll, or folded format in a dispenser outside or suspended in the spa. If the ratio of certain chemicals such as bromine/chlorine, or chlorine/pH modifier is known, the chemicals can be sealed into adjacent different compartments in the polymeric film and dispensed simultaneously or consecutively by for example interspacing pH modifier packet every 25 LH packets.

In yet another embodiment, chemicals can also be mixed into a gel or a paste for example lithium hypochlorite and propylene glycol and placed in a large sealed polymeric bag which can be placed in dispensing unit 12.

Scent chemicals can be automatically dispensed in a powder or liquid form in response to usage in a similar manner.

Table 1 below lists examples of various chemicals and dispensing forms which can be used with the present invention.

TABLE 1

| | Chemicals | | | | |
|---|---|---|---|---|---|
| Chemistry | Any | DiChlor | Lithium Hypochlorite | Lithium Hypochlorite | Bromine/Dichlor |
| Storage | dry powder | dry granules | dry powder | Gel | hydrated granules |
| In-use format | in a bulk cartridge with a dispensing cap | hydrated granules in cartridge | dry powder in strip of blister packets | Pinch rollers on a polymeric bag with a one way valve to keep water from entering bag | hydrated granules in cartridge |
| dispensing system | DC motor with current | water pump | Puncture mechanism | | simple water pump |

TABLE 1-continued

| | | | Chemicals | | |
|---|---|---|---|---|---|
| Chemistry | Any | DiChlor | Lithium Hypochlorite | Lithium Hypochlorite | Bromine/Dichlor |
| | sensing | | with stepper motor pull | | |
| Storage | Cartridge | Cartridge | linked single packets | | |
| Shipping classification | 2 | 2 | 2 | 2 | 2 |
| Available sanitizer (% Available Chlorine) | 35% or more | 55% | 35% | 35% | NA |
| start up package | As needed | CA, TA | CA, Boric acid (to lower TA), CYA | | CA, TA, bromine salt |
| TA issues | As needed | TA drops; need to compensate | keep TA low | Keep TA low | TA drops; need to compensate |
| pH issues | As needed | | Requires low TA to keep pH stable | Requires low TA to keep pH stable | low pH will counter up drift of spa |
| Risks | As applicable | CYA build up | must be kept dry until dispensed, gas must be vented | | |

The present system can alternatively use chemical generators rather than dispense stored chemicals. Examples of chemical generators that can be used by the present system include, but are not limited to, the TechniChlor, MiniChlor or ColorChlor Hot Tub and Spa Chlorine Generators (www.controlomatic.com/technichlor.html) and the NexaSpa Plug-In Natural Chlorine Generator (images.spadepot.com/docs/nexa-chlor.pdf).

Water Chemistry Assessment

In addition to anticipating spa water condition from use, system 10 can also include sensors for measuring the chemistry of spa water. For example, system 10 can utilize a miniature oxidation reduction potential (ORP) (such as those made by Hanna Instruments) as a correlate of chlorine or bromine level in the water.

Alternatively, system 10 can utilizes a carrier roll of filter paper pads each with colorimetric chemistry that changes color in response to the level of an analyte in the water such as oxidizer level, pH, total alkalinity, hardness, etc. System 10 exposes each pad or sets of pads to spa water and uses a photo detector with illuminator to analyze the color or a CCD camera to capture an image of the pad(s), color adjust it based on a nearby color reference and then determine the exact color of each pad which correlates to the level of analyte it he water. The analysis can also be carried out via a photo detector or camera of system 10 in response to a commercially available dip stick that the user dunks in the spa water and then places into system 10 for analysis. Alternatively, a user can use a smartphone to take a picture of the dip stick and analyze the resulting image. The results can be transmitted to system 10 via a Bluetooth link or the like.

Algorithm

Figure 7:
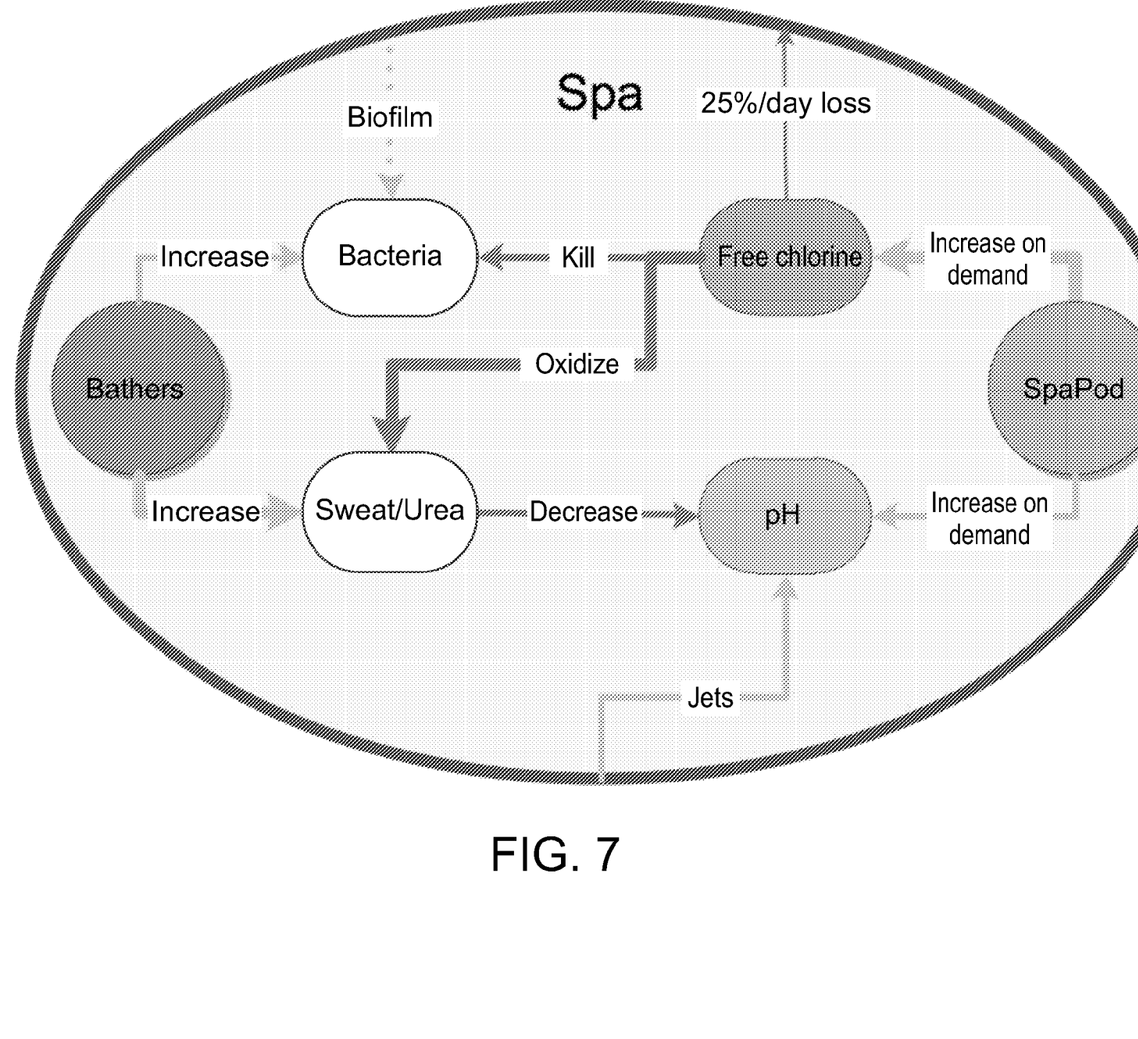
FIG. 7 outlines the challenges of controlling the sanitizer level and pH in spa water.

The processor of system 10 can execute an algorithm which is configured for minimizing chemical consumption while maintaining the spa water clear, fresh smelling and sanitary. The challenges of maintaining spa water sanitized yet fresh smelling and 'soft' are outlined in FIG. 7.

If no usage, estimate background chlorine loss and make it up at the beginning filter cycle to maintain chlorine level at 2 ppm. If usage occurred, estimate the time used (and if possible number of people) and dose chlorine when they leave the spa to make up for likely chlorine loss. If dosing is likely to raise chlorine above 5 ppm alert the user in order to discourage spa usage until chlorine level is estimated drop to acceptable levels. System 10 keeps track of spa usage and recommends water change based on the volume in gallons divided by 3 divided by the number of individuals using the spa for 20 minute sessions. Keep track of spa usage and request an occasional sanitizer/pH check via stick and Bluetooth smartphone application (as described above). Adjust background chlorine usage calculations based on the anticipated vs. measured chlorine level. Instruct the user to dispense the appropriate pH up or pH down packets as indicated by the test. Try to estimate pH up need based on usage of the jets based on accelerometer data. If the spa has an ozonator, its effectiveness will be a function of the filter run time.

The Bluetooth link can be used to receive information about spa usage (e.g. unauthorized use), chemical usage and anticipated remaining time for the cartridge(s), extrapolate energy consumption (user enters motor and heater size), chemistry adjustments over time and chemical consumption.

Thus, the present invention provides a system which can be used to monitor and control the water chemistry of a recreational water installation such a spa. The present system is advantageous in that it minimizes use of chemicals by adjusting water chemistry based on actual need and usage and not based on scheduling.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Sound as a Measure of Spa Use

Figure 8A:
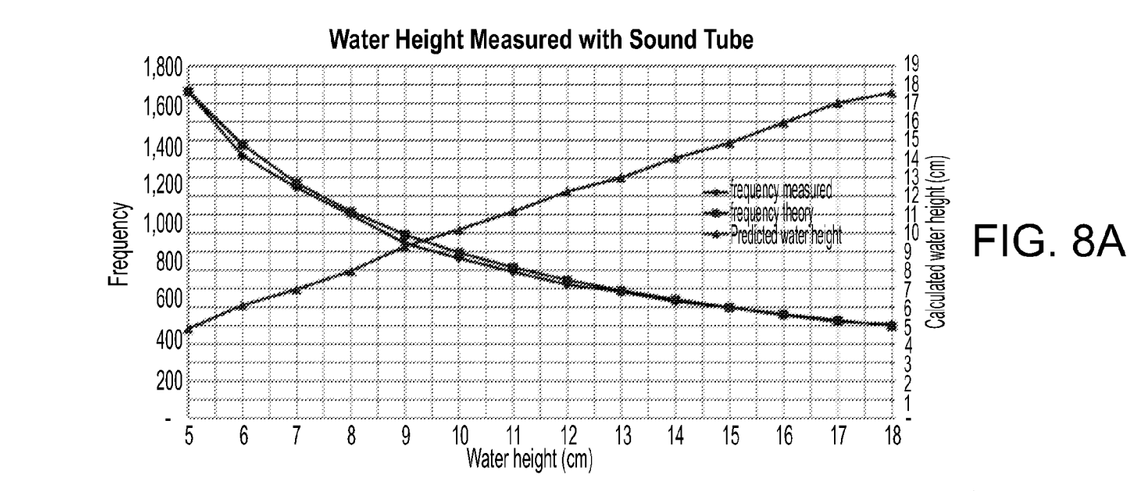
FIGS. 8A-B illustrate graphed data (FIG. 8A) from a theoretical sound tube model as well as actual sound measurements (FIG. 8B) collected from a hot tub.
Figure 8B:
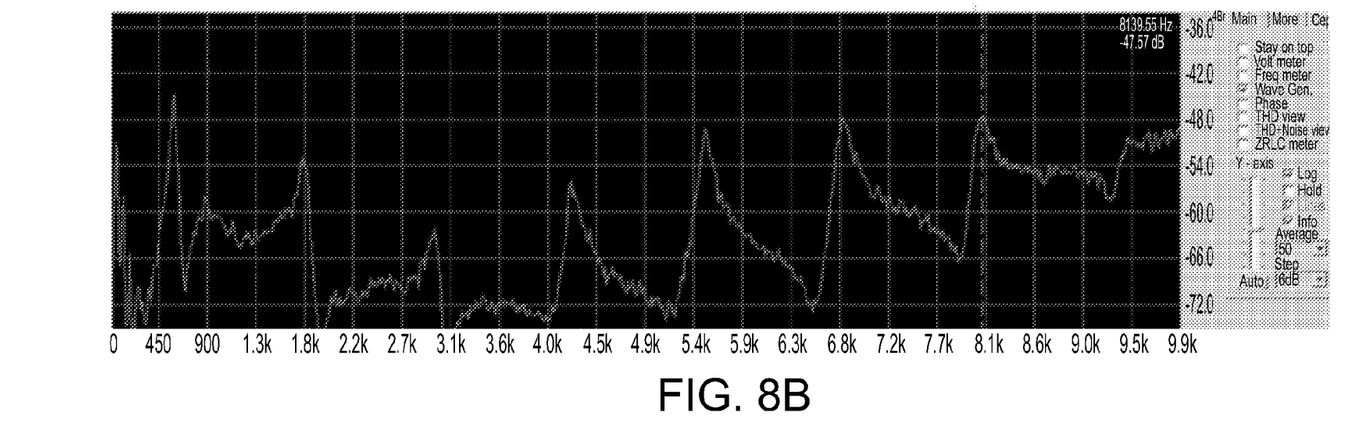

An electret microphone was attached near one end of a plastic tube with 13 mm ID and connected to the microphone input of a PC running data recording and FFT software (Visual Analyzer). A 12 mm diameter speaker was fixed at the end of the tube and connected to a white noise generator. The tube was attached to the side of a spa such that its open end was contacting the water. The water was raised as FFT spectrum was captured (FIG. 8b). Each spectrum was analyzed for the resonant frequency peaks. The difference in frequency between the peaks was calculated and converted to the water height in the sound tube. The graph in FIG. 8a shows the measured frequency, the theoretical frequency and the calculated water height versus the measured water height in the sound tube.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for controlling water chemistry of a recreational water installation, comprising:
    a sensor configured to detect bather load in the recreational water installation;
    a controller configured to determine a required adjustment to the water chemistry of the recreational water installation based upon the detected bather load;
    a plurality of individual packets arranged in a strip, each packet containing a chemical dose unit and each packet being individually sealed within a water barrier film; and
    a dispenser configured to dispense the chemical dose unit from one of the plurality of packets into the recreational water installation based upon the determined required adjustment, wherein the dispenser comprises a packet disruption mechanism configured to disrupt each packet and dispense its contents, wherein the dispenser comprises a motor operatively connected to the strip and adapted to move the strip with respect to the packet disruption system.

2. The system of claim 1, wherein the controller is configured to automatically dispense a chemical dose unit from the dispenser based upon the determined required adjustment.

3. The system of claim 2, wherein the controller is configured to dispense a chemical dose unit only when there are no detected bathers in the recreational water installation.

4. The system of claim 1, wherein the controller is configured to alert a user of the determined required adjustment.

5. The system of claim 4, further comprising a user interface, the user interface configured to display the determined required adjustment.

6. The system of claim 1, wherein the sensor is configured to detect a change in water level of the recreational water installation.

7. The system of claim 1, wherein the sensor and the controller are part of a unit configured to sit within the water installation.

8. The system of claim 7, further comprising a transmitter attached to the unit, the transmitter configured to wirelessly communicate information from the controller.

9. The system of claim 1, wherein the recreational water installation is a spa.

10. The system of claim 1, further comprising a sensor configured to detect the water chemistry, the controller further configured to determine the required adjustment based upon the detected chemistry.

11. The system of claim 1, wherein the controller is further configured to record use patterns.

12. The system of claim 11, wherein the controller is further configured to predict and alert when water in the recreational water installation should be replenished or replaced based upon the use patterns.

13. A system for controlling water condition of a water installation, comprising:
    a sensor configured to detect a water condition of the water installation;
    a controller configured to determine a required adjustment to the water chemistry of water installation based upon the detected water condition; and
    a dispenser comprising a packet disruption mechanism configured to dispense chemicals from one of a plurality of packets, each packet separately sealed within a water barrier film, into the water installation based upon the determined required adjustment, wherein the dispenser further comprises a motor adapted to move a strip of a plurality of packets sealed within a water barrier film with respect to the packet disruption mechanism.

14. The system of claim 13, wherein the water condition is bather load.

15. The system of claim 13, wherein the sensor comprises a colorimetric sensor.

16. The system of claim 15, wherein the colorimetric sensor comprises an element configured to change color in response to the level of an analyte in the water installation and a detector to analyze a color change of the element.

* * * * *